United States Patent
Alobaid

(10) Patent No.: US 8,900,304 B1
(45) Date of Patent: Dec. 2, 2014

(54) KYPHOPLASTY CEMENT ENCAPSULATION BALLOON

(71) Applicant: Abdulrazzaq Alobaid, Kuwait (KW)

(72) Inventor: Abdulrazzaq Alobaid, Kuwait (KW)

( * ) Notice: Subject to any disclaimer, the term of this patent is extended or adjusted under 35 U.S.C. 154(b) by 0 days.

(21) Appl. No.: 14/307,410

(22) Filed: Jun. 17, 2014

(51) Int. Cl.
| A61F 2/44 | (2006.01) |
| A61B 17/88 | (2006.01) |
| A61B 17/70 | (2006.01) |
| A61B 17/00 | (2006.01) |

(52) U.S. Cl.
CPC ......... *A61B 17/7094* (2013.01); *A61B 17/8855* (2013.01); *A61B 2017/00557* (2013.01)
USPC ........................................ 623/17.12; 606/92

(58) Field of Classification Search
CPC ........... A61B 17/7097; A61B 17/7098; A61B 17/8811; A61B 17/8855; A61F 2/441
USPC ................... 606/326, 327, 86 R, 92–94, 105; 623/17.12, 23.62; 604/99.01–99.04
See application file for complete search history.

(56) References Cited

U.S. PATENT DOCUMENTS

| 4,364,392 A | | 12/1982 | Strother et al. | |
| 4,697,584 A | * | 10/1987 | Haynes | 606/95 |
| 5,181,921 A | * | 1/1993 | Makita et al. | 606/195 |
| 5,849,014 A | * | 12/1998 | Mastrorio et al. | 606/94 |
| 6,855,153 B2 | | 2/2005 | Saadat | |
| 6,960,215 B2 | | 11/2005 | Olson, Jr. et al. | |
| 7,591,822 B2 | * | 9/2009 | Olson et al. | 606/93 |
| 2002/0147497 A1 | * | 10/2002 | Belef et al. | 623/17.12 |
| 2004/0210297 A1 | * | 10/2004 | Lin et al. | 623/1.11 |
| 2008/0103505 A1 | | 5/2008 | Fransen | |
| 2009/0312807 A1 | | 12/2009 | Boudreault et al. | |
| 2011/0112588 A1 | * | 5/2011 | Linderman et al. | 606/86 R |
| 2014/0012307 A1 | | 1/2014 | Franano et al. | |
| 2014/0207193 A1 | * | 7/2014 | Druma | 606/279 |

* cited by examiner

*Primary Examiner* — Michael T. Schaper
*Assistant Examiner* — Amy Sipp
(74) *Attorney, Agent, or Firm* — Richard C Litman

(57) ABSTRACT

The kyphoplasty cement encapsulation balloon is a flexible, resilient silicone balloon having a catheter or filling tube disposed inside the balloon. The filling tube has a closed end and a plurality of orifices defined in the tube radially. The tube has an open mouth extending through a hole in the balloon, defining an inflation port. The inflation port is internally threaded, and preferably has a radiopaque marker band extending around the port. The inflation port has a one-way duck or duckbill valve that closes the inflation port when the inflation cannula is detached from the port, thereby encapsulating the bone cement in the balloon and preventing leakage of the cement. The inflation cannula and the kyphoplasty cement encapsulation balloon may be furnished as a kit.

13 Claims, 7 Drawing Sheets

KYPHOPLASTY CEMENT ENCAPSULATION BALLOON

BACKGROUND OF THE INVENTION

1. Field of the Invention

The present invention relates to devices for performing kyphoplasty, and particularly to a kyphoplasty cement encapsulation balloon for encapsulating cement inserted into a cavity in a vertebra during a kyphoplasty.

2. Description of the Related Art

Kyphoplasty is a contemporary balloon-assisted vertebroplasty alternative for treatment of vertebral body compression fracture (VCF). Kyphoplasty involves injection of bone cement into a mechanically created bone void within a vertebral body. A balloon is first inserted into the structurally compromised vertebral body, often through a cannula. The balloon is then inflated under high pressure. It is claimed that the expanding balloon disrupts the cancellous bone architecture and physiological matrix circumferentially and directs the attendant bony debris and physiologic matrix toward the inner cortex of the vertebral body vault, i.e., restores the height of the vertebra. The balloon is then deflated and removed, leaving a bony void or cavity. The remaining void or cavity is repaired by filling it with an appropriate biomaterial media, most often bone cement, usually polymethylmethacrylate (PMMA). In most cases, the treatment goals are to reduce or eliminate pain and the risk of progressive fracture of the vertebral body and its likely resulting morbidity, complications, and disability.

A common risk of balloon kyphoplasty is leakage of the PMMA from the cavity, which may cause nerve injury, infection, numbness, or spinal cord compression, or may require corrective procedures resulting from leakage of the cement. Thus, a kyphoplasty cement encapsulation balloon solving the aforementioned problems is desired.

SUMMARY OF THE INVENTION

The kyphoplasty cement encapsulation balloon is a flexible, resilient silicone balloon having a catheter or filling tube disposed inside the balloon. The filling tube has a closed end and a plurality of orifices defined in the tube radially. The tube has an open mouth extending through a hole in the balloon, defining an inflation port. The inflation port is internally threaded, and preferably has a radiopaque marker band extending around the port. The inflation port has a one-way duck or duckbill valve that closes the inflation port when the inflation cannula is detached from the port, thereby encapsulating the bone cement in the balloon and preventing leakage of the cement. The inflation cannula and the kyphoplasty cement encapsulation balloon may be furnished as a kit.

In use, the kyphoplasty balloon is inserted into the vertebra needing repair, inflated to correct the alignment of the vertebra, deflated, and removed, as in conventional kyphoplasty procedures. An inflation cannula having an externally threaded end is attached to the inflation port of the cement encapsulation balloon, and the cement encapsulation balloon is inserted into the cavity formed in the vertebra using radiographic imaging to position the device. Kyphoplasty cement is inserted into the cement encapsulation balloon through the inflation cannula, being pushed through the orifices in the catheter or filling tube, thereby inflating the cement encapsulation balloon. When the desired quantity of cement has been injected into the cement encapsulation balloon, the inflation cannula is detached from the inflation port by unthreading the cannula, leaving the filling tube encapsulated in the cement inside the tube. The duckbill valve automatically closes when the cannula is detached and removed, preventing the kyphoplasty cement from leaking out of the cavity and closing the mouth of the filling tube, whereby the kyphoplasty cement is encapsulated in the kyphoplasty cement encapsulation balloon.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The kyphoplasty cement encapsulation balloon is a flexible, resilient silicone balloon having a catheter or filling tube disposed inside the balloon. The filling tube has a closed end and a plurality of orifices defined in the tube radially. The tube has an open mouth extending through a hole in the balloon, defining an inflation port. The inflation port is internally threaded, and preferably has a radiopaque marker band extending around the port. The inflation port has a one-way duck or duckbill valve that closes the inflation port when the inflation cannula is detached from the port, thereby encapsulating the bone cement in the balloon and preventing leakage of the cement. The inflation cannula and the kyphoplasty cement encapsulation balloon may be furnished as a kit.

In use, the kyphoplasty balloon is inserted into the vertebra needing repair, inflated to correct the alignment of the vertebra, deflated, and removed, as in conventional kyphoplasty procedures. An inflation cannula having an externally threaded end is attached to the inflation port of the cement encapsulation balloon, and the cement encapsulation balloon is inserted into the cavity formed in the vertebra using radiographic imaging to position the device. Kyphoplasty cement is inserted into the cement encapsulation balloon through the inflation cannula, being pushed through the orifices in the catheter or filling tube, thereby inflating the cement encapsulation balloon. When the desired quantity of cement has been injected into the cement encapsulation balloon, the inflation cannula is detached from the inflation port by unthreading the cannula, leaving the filling tube encapsulated in the cement inside the tube. The duckbill valve automatically closes when the cannula is detached and removed, preventing the kyphoplasty cement from leaking out of the cavity and closing the mouth of the filling tube, whereby the kyphoplasty cement is encapsulated in the kyphoplasty cement encapsulation balloon.

Figure 1:
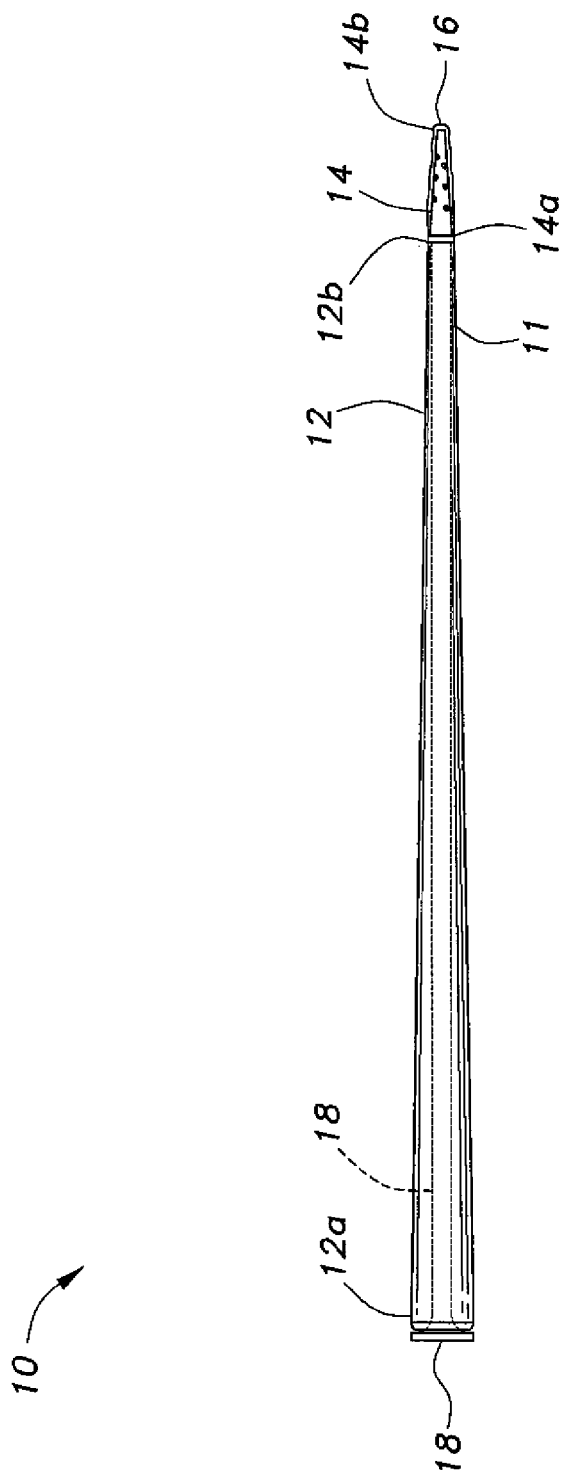
FIG. 1 is a front view of a kyphoplasty cement encapsulation balloon according to the present invention, shown as an assembly with the inflation cannula attached and the balloon broken away to show the catheter or filling tube.
Figure 2:
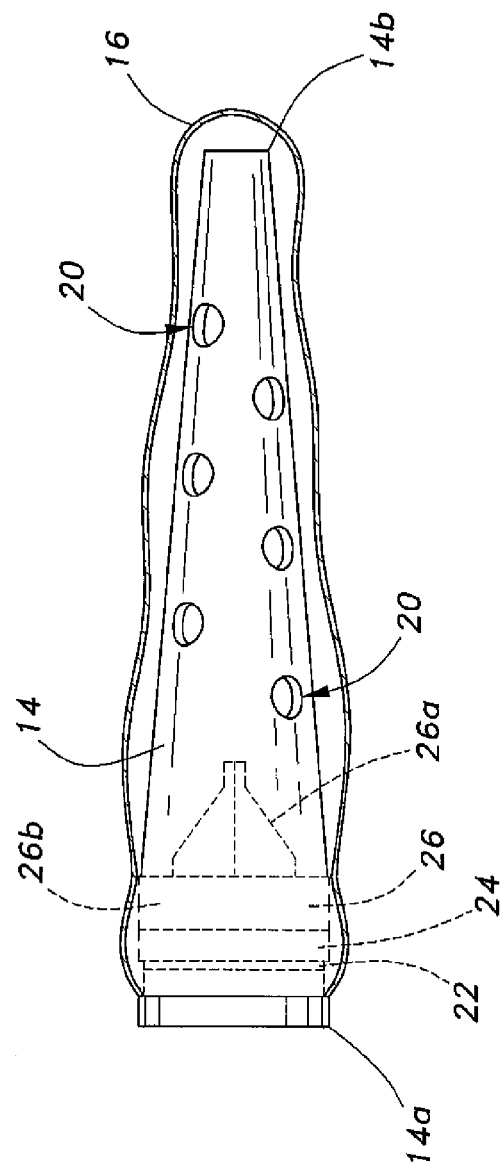
FIG. 2 is a front view of the kyphoplasty cement encapsulation balloon of FIG. 1, shown with the balloon in section.

An exemplary kyphoplasty cement encapsulation balloon assembly, generally designated as 10, is shown in FIG. 1. The kyphoplasty cement encapsulation balloon assembly 10 is a generally tubular body 11, including an inflation cannula 12 and a kyphoplasty cement encapsulation balloon 16 that are detachably connected. The inflation cannula 12 has a proximal end 12a and a distal end 12b. The kyphoplasty cement encapsulation balloon 16 includes a catheter or filling tube 14 having a proximal end 14a and a distal end 14b. The distal end 12b of the inflation cannula 12 may be detachably connected to the proximal end 14a of the filling tube 14. A plunger 18 may be disposed in an interior or lumen of the inflation cannula 12. The plunger 18 may be configured for slidable movement within the lumen of the inflation cannula 12.

The kyphoplasty cement encapsulation balloon 16 is a balloon 16 made of biocompatible material, preferably made of silicone. The balloon 16 is preferably resilient, but may be a non-resilient pouch of flexible material having an open end that is attached at or near the proximal end 14a of the filling tube 14. The filling tube 14 has a sealed distal end 14b and a plurality of orifices 20 defined in the tube radially. Preferably, the orifices 20 extend around a circumference of the filling tube. The proximal end 14a of the filling tube 14 defines an inflation port having an open mouth. A radiopaque marker 22 band may be positioned along a circumferential portion of the proximal end 14a. The radiopaque marker band 22 may be formed from metal to facilitate visibility under an x-ray fluoroscope.

The kyphoplasty cement encapsulation balloon 16 may include one or more one-way valves to prevent backflow of the bone cement. The filling tube 14 may include a first one-way valve 24 and a second one-way valve 26 connected thereto. The first one-way valve 24 may be any suitable type of check valve. The second one-way valve 26 is preferably a duckbill valve. The duckbill valve 26 has a flattened, beak portion 26a and a round connecting end 26b. The connecting end 26b of the duckbill valve may be stretched over an end of the first one-way valve 24, and expands over the inflation port at the proximal end 14a when the inflation cannula 12 is detached.

When bone cement is introduced into the lumen of the inflation cannula 12, a plunger 18 may be used to move the bone cement through the lumen. For example, bone cement may be forced through the first one-way valve 24 and the second one-way valve 26 with the plunger 18. The beak portion 26a of the duckbill valve opens to permit the bone cement to pass. After the bone cement has passed through the beak portion 26a, the beak portion 26a returns to its flattened shape to prevent backflow. The bone cement flows into the balloon 16 through the plurality of orifices 20.

Figure 3:
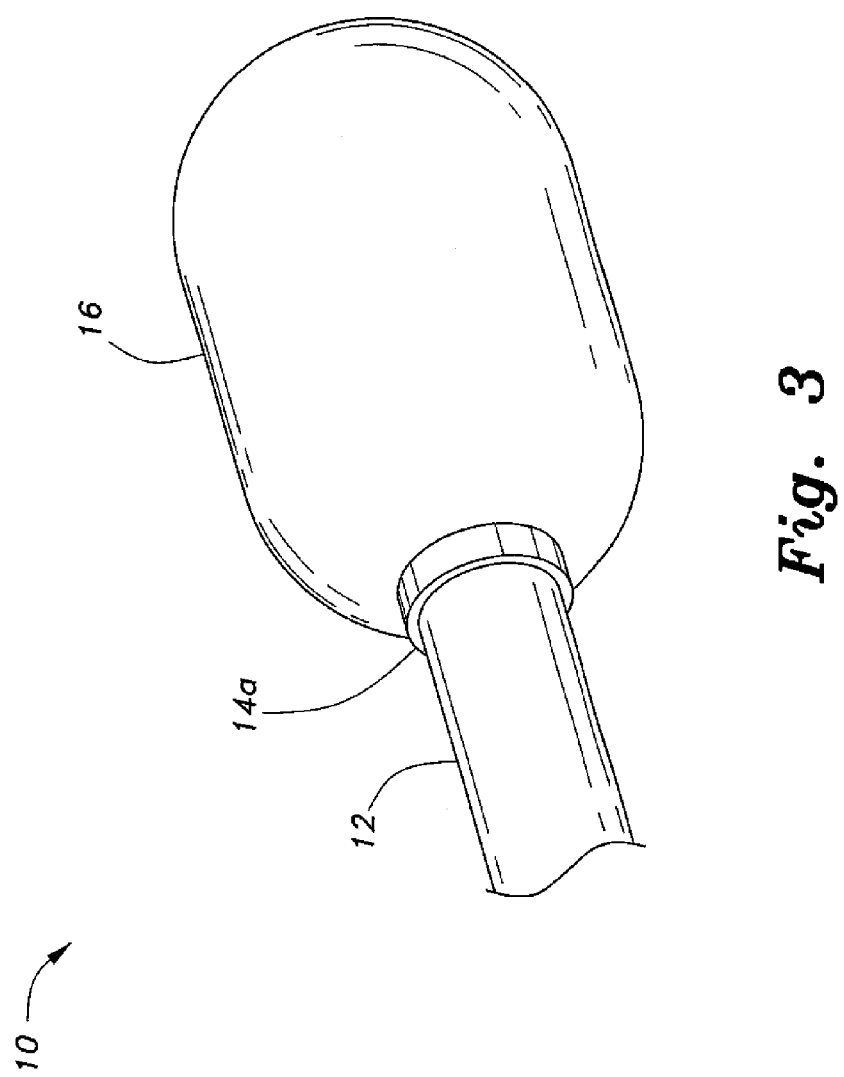
FIG. 3 is a partial perspective view of the kyphoplasty cement encapsulation balloon assembly of FIG. 1, showing the expandable material in an expanded state.

The balloon 16 is configured to expand or swell as it is filled with the bone cement, as shown in FIG. 3. The balloon 16 may be formed from any suitable, expandable material that is biocompatible. The balloon 16 may be formed from a biocompatible polymeric material. The balloon 16 may be a silicone balloon, for example. An end or neck portion of the balloon 16 may be attached at or adjacent to the proximal end 14a of the filling tube 14.

Figure 4:
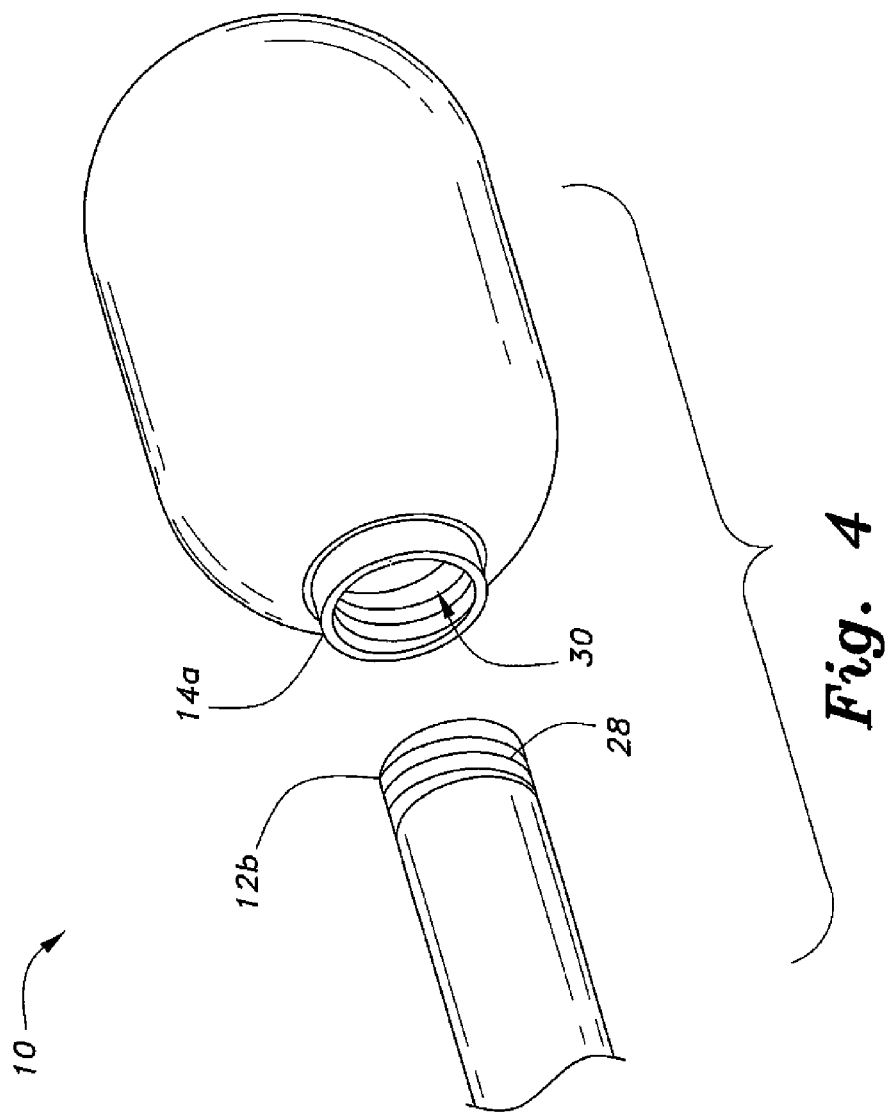
FIG. 4 is a partial perspective view of the kyphoplasty cement encapsulation balloon assembly of FIG. 1, showing the showing the inflation cannula detached from the balloon.

As described previously, the inflation cannula 12 and the catheter or filling tube 14 may be detachably connected. Any suitable connection means may be used to facilitate detachable connection of the inflation cannula 12 and the catheter or filling tube 14. As shown in FIG. 4, for example, the distal end 12b of the inflation cannula 12 and the proximal end 14a of the filling tube 14 may include threaded portions 28 and 30, respectively, for detachably connecting the inflation cannula 12 and the catheter or filling tube 14. The inflation cannula 12 may be twisted off of the filling tube 14 for detachment.

The catheter or filling tube 14 may be formed from a biocompatible material. For example, the filling tube 14 may be made from an implantable-grade biomaterial, such as a regulatory-approved stainless steel, polymer, or ceramic.

Figure 5:
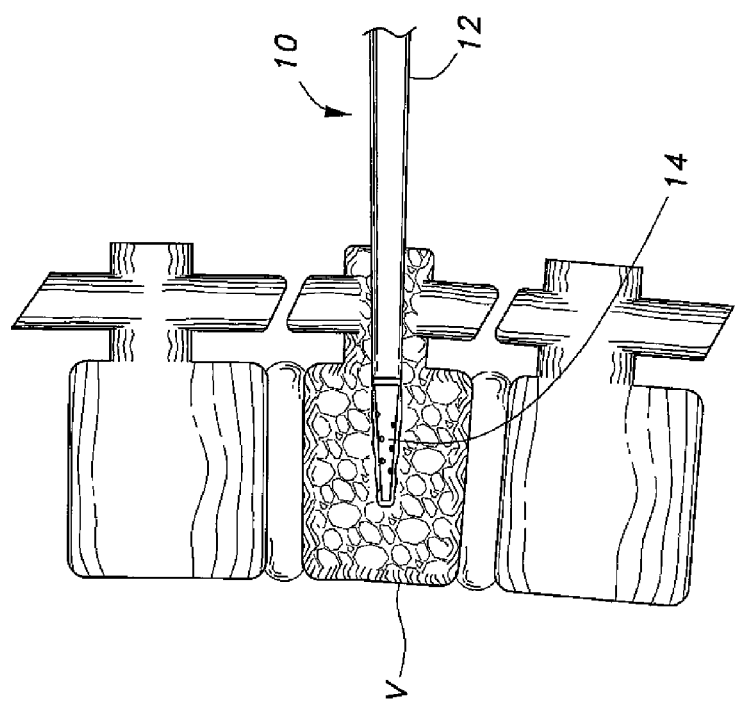
FIG. 5 is an environmental perspective view of a kyphoplasty cement encapsulation balloon according to the present invention, showing the balloon being positioned within the cavity formed in a compressed vertebral body.
Figure 6:
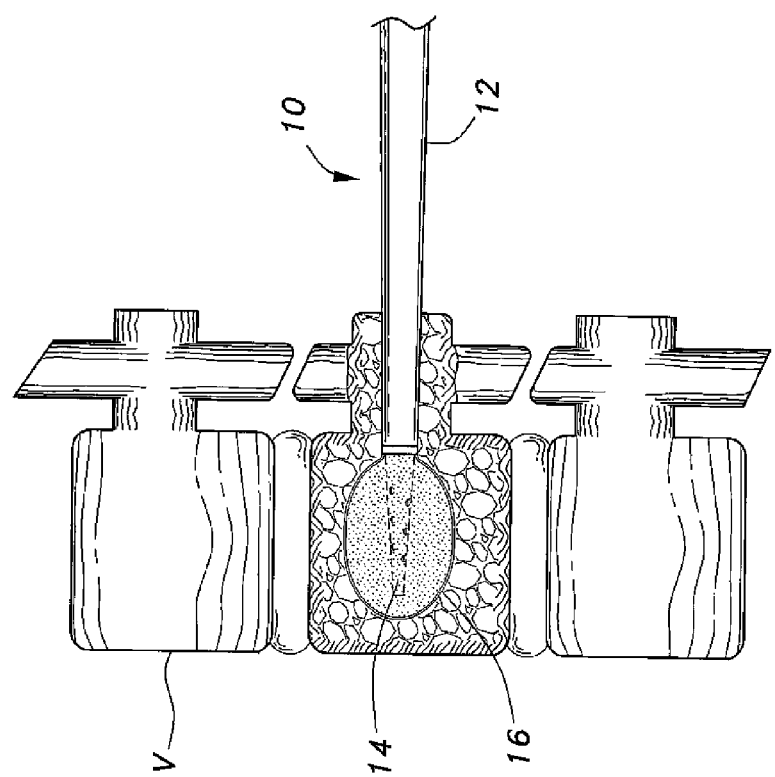
FIG. 6 is an environmental perspective view of the kyphoplasty cement encapsulation balloon of FIG. 5, showing the balloon inflated by the kyphoplasty cement within the vertebral body.
Figure 7:
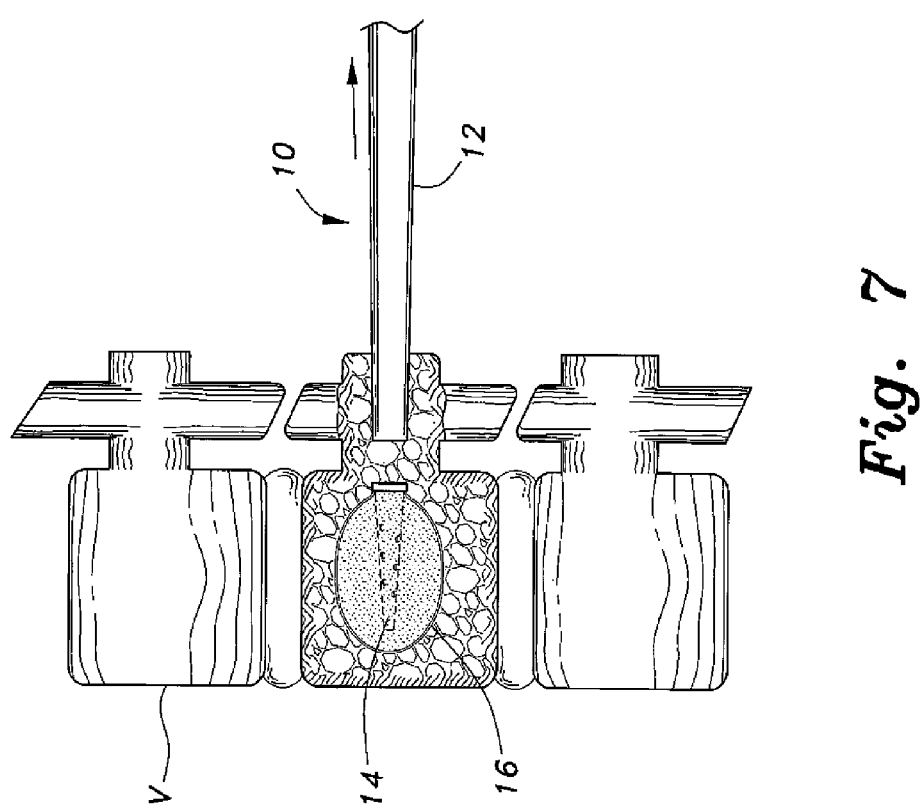
FIG. 7 is an environmental perspective view of the kyphoplasty cement encapsulation balloon of FIG. 5, showing the inflation cannula being removed from the vertebral body.

FIGS. 5-7 depict an exemplary method for using the kyphoplasty cement encapsulation balloon 16. The kyphoplasty cement encapsulation balloon assembly 10 may access a treatment site of the vertebral body V using any suitable approach typically used in kyphoplasty and/or vertebroplasty, e.g., a transpedicular or extrapedicular approach may be used. The filling tube 14 may be positioned within a void or cavity in a damaged or compressed vertebral body V, as shown in FIG. 5. Bone cement introduced into the inflation cannula 12 may be dispensed into the balloon 16 through the plurality of orifices 20 in the implantable portion, causing the expandable material to expand or swell in order to accommodate the bone cement, as shown in FIG. 6. In its expanded state, the balloon 16 may conform to a cavity of the vertebral body in which it is positioned. As shown in FIG. 7, the inflation cannula 12 may be detached from the filling tube 14 and removed from the vertebral body V once the balloon 16 is filled with the bone cement. The filling tube 14 and the bone cement are encapsulated within the balloon 16 so that they may remain in the vertebral body V.

It is to be understood that the present invention is not limited to the embodiments described above, but encompasses any and all embodiments within the scope of the following claims.

I claim:

1. A kyphoplasty kit, comprising:
    an expandable body defining an encapsulation balloon made from a biocompatible material;
    an elongated filling tube having a proximal end, a distal end being a free end, and a plurality of radially distributed orifices defined in the tube, the distal end being sealed, the proximal end being open and defining an inflation port, the filling tube being disposed within the balloon and the inflation port extending through the balloon;
    a one-way valve disposed to close the open end of the filling tube; and
    an inflation cannula detachably connectable to the inflation port;
    wherein kyphoplasty cement is inserted into the balloon by dispersion via the orifices of the filling tube, and upon the closing of the one-way valve prevents leakage of kyphoplasty cement from the balloon, the filling tube and the kyphoplasty cement being encapsulated permanently within the balloon when the encapsulation balloon is implanted in a vertebra.

2. The kyphoplasty kit according to claim 1, further comprising a radiopaque marker band disposed around the inflation port.

3. The kyphoplasty kit according claim 1, wherein the expandable body is made from silicone.

4. The kyphoplasty kit according to claim 1, wherein the one-way valve comprises a duckbill valve.

5. The kyphoplasty kit according to claim 1, wherein the inflation port is internally threaded.

6. The kyphoplasty kit according to claim 5, wherein the cannula has a proximal end and a distal end, the distal end being externally threaded, the threaded distal end of the cannula releasably engaging the internally threaded inflation port, whereby the cannula is detachable from the balloon.

7. The kyphoplasty kit according to claim 6, further comprising a plunger slidable in the proximal end of the inflation cannula.

8. A kyphoplasty kit, comprising:
   an expandable body defining an encapsulation balloon made from a biocompatible material;
   a catheter having a proximal end, a distal end as a free end, and a plurality of radially distributed orifices defined in the catheter, the distal end being sealed, the proximal end being open and defining an inflation port, the catheter being disposed within the balloon and the inflation port extending through the balloon;
   a duckbill valve disposed to close the open end of the catheter and prevent leakage of kyphoplasty cement from the balloon, the catheter and the kyphoplasty cement being permanently encapsulated within the balloon when the balloon is implanted in a vertebra; and
   an inflation cannula detachably connectable to the inflation port.

9. The kyphoplasty kit according to claim 8, wherein:
   the inflation port is internally threaded; and
   the cannula has a proximal end and a distal end, the distal end being externally threaded and connectable to the inflation port.

10. The kyphoplasty kit according to claim 8, wherein the expandable body is made from silicone.

11. The kyphoplasty kit according to claim 8, further comprising a radiopaque marker band disposed around the inflation port.

12. The kyphoplasty kit according to claim 8, further comprising a plunger slidable in the inflation cannula.

13. A method of performing kyphoplasty, comprising the steps of:
   inserting a cavity-forming balloon into a vertebral body;
   inflating the cavity-forming balloon to form a cavity in the vertebral body;
   removing the cavity-forming balloon from the vertebral body;
   inserting a kyphoplasty cement encapsulation balloon into the cavity in the vertebral body, the kyphoplasty cement encapsulation balloon having a porous catheter having a free distal end extending within the balloon;
   injecting kyphoplasty cement through an inflation cannula connected to a proximal end of the porous catheter into the kyphoplasty cement encapsulation balloon in order to inflate the balloon to fill the cavity;
   wherein the porous catheter allows the kyphoplasty cement to be distributed throughout the kyphoplasty cement encapsulation balloon, thereby filling the cavity in the vertebral body;
   detaching the inflation cannula from the porous catheter, the kyphoplasty cement encapsulation balloon having a one-way valve preventing leakage of the kyphoplasty cement from the encapsulation balloon;
   removing the inflation cannula from the vertebral body; and
   leaving the kyphoplasty cement encapsulation balloon in the vertebral body permanently, the kyphoplasty cement and the porous catheter being encapsulated within the balloon.

* * * * *